United States Patent
Dowling

(10) Patent No.: US 12,403,157 B2
(45) Date of Patent: Sep. 2, 2025

(54) SYSTEM AND METHOD TO REDUCE TISSUE ORORGAN ADHESION

(71) Applicant: Medcura, Inc., Riverdale, MD (US)

(72) Inventor: Matthew B. Dowling, Riverdale, MD (US)

(73) Assignee: Medcura, Inc., Riverdale, MD (US)

( * ) Notice: Subject to any disclaimer, the term of this patent is extended or adjusted under 35 U.S.C. 154(b) by 998 days.

(21) Appl. No.: 17/436,597

(22) PCT Filed: Mar. 4, 2020

(86) PCT No.: PCT/US2020/021039
§ 371 (c)(1),
(2) Date: Sep. 4, 2021

(87) PCT Pub. No.: WO2020/181015
PCT Pub. Date: Sep. 10, 2020

(65) Prior Publication Data
US 2022/0168334 A1 Jun. 2, 2022

Related U.S. Application Data

(60) Provisional application No. 62/814,265, filed on Mar. 5, 2019.

(51) Int. Cl.
| | | |
|---|---|---|
| *A61K 31/727* | (2006.01) | |
| *A61K 31/722* | (2006.01) | |
| *A61L 31/04* | (2006.01) | |
| *A61L 31/06* | (2006.01) | |
| *A61L 31/14* | (2006.01) | |
| *A61L 31/16* | (2006.01) | |

(52) U.S. Cl.
CPC .......... *A61K 31/722* (2013.01); *A61L 31/042* (2013.01); *A61L 31/06* (2013.01); *A61L 31/146* (2013.01); *A61L 31/148* (2013.01); *A61L 31/16* (2013.01); *A61L 2300/404* (2013.01); *A61L 2400/06* (2013.01)

(58) Field of Classification Search
None
See application file for complete search history.

(56) References Cited

U.S. PATENT DOCUMENTS

| | | |
|---|---|---|
| 4,532,134 A | 7/1985 | Malette et al. |
| 4,572,906 A | 2/1986 | Sparkes et al. |
| 4,645,757 A | 2/1987 | Hjerten et al. |
| 4,752,466 A | 6/1988 | Saferstein et al. |
| 4,895,724 A | 1/1990 | Cardinal et al. |
| 5,243,094 A | 9/1993 | Borg |
| 5,426,182 A | 6/1995 | Jenkins et al. |
| 5,900,479 A | 5/1999 | Glasser et al. |
| 5,919,574 A | 7/1999 | Hoagland |
| 6,140,089 A | 10/2000 | Aebischer et al. |
| 6,371,975 B2 | 4/2002 | Cruise et al. |
| 6,458,147 B1 | 10/2002 | Cruise et al. |
| 6,548,081 B2 | 4/2003 | Sadozai et al. |
| 6,602,952 B1 | 8/2003 | Bentley et al. |
| 6,663,653 B2 | 12/2003 | Akerfeldt |
| 6,827,727 B2 | 12/2004 | Stalemark et al. |
| 6,830,756 B2 | 12/2004 | Hnojewyj |
| 6,864,245 B2 | 3/2005 | Vournakis et al. |
| 6,890,344 B2 | 5/2005 | Levinson |
| 6,899,889 B1 | 5/2005 | Hnojewyj et al. |
| 6,949,114 B2 | 9/2005 | Milo et al. |
| 6,958,325 B2 | 10/2005 | Domb |
| 6,994,686 B2 | 2/2006 | Cruise et al. |
| 6,995,137 B2 | 2/2006 | You et al. |
| 7,247,314 B2 | 7/2007 | Hnojewyj et al. |
| 7,279,001 B2 | 10/2007 | Addis et al. |
| 7,288,532 B1 | 10/2007 | Payne et al. |
| 7,318,933 B2 | 1/2008 | Hnojewyj |
| 7,351,249 B2 | 4/2008 | Hnojewyj et al. |
| 7,482,503 B2 | 1/2009 | Gregory et al. |
| 7,820,872 B2 | 10/2010 | Gregory et al. |
| 8,664,199 B2 | 3/2014 | Dowling et al. |

(Continued)

FOREIGN PATENT DOCUMENTS

| | | |
|---|---|---|
| DE | 19629248 A1 | 1/1997 |
| EP | 1222926 | 7/2002 |

(Continued)

OTHER PUBLICATIONS

Zhdanov et al. Adsorption and Spontaneous Rupture of Vesicles Composed of Two Types of Lipids (Langmuir 2006, 22, 3477-3480).

Yoshina-Ishii et al., Diffusive Dynamics of Vesicles Tethered to a Fluid Supported Bilayer by Single-Particle Tracking, Langmuir 22(13):5682-5689 (2006).

Yoshina-Ishii et al., General Method for Modification of Liposomes for Encoded Assembly on Supported Bilayers, J. Am. Chem. Soc. 127(5):1356-1357 (2005).

Zhang, Jing. Drug Delivery: Self-Assembled Nanoparticles based on Hydrophobically Modified chitosan as Carriers for Doxorubicin, Nanomedicine, Elsevier. Aug. 2007. pp. 258-265.

Kheirabadi, Bijan S. et al., Hemostatic Efficacy of Two Advanced Dressings in an Aortic Hemorrhage Model in Swine, J. Trauma Injury, Infection, and Critical Care, 59:25-35 (2005).

(Continued)

*Primary Examiner* — Traviss C McIntosh, III

(74) *Attorney, Agent, or Firm* — The Morales Law Firm; Joseph L. Morales, Esq.

(57) ABSTRACT

A composition for providing a barrier between tissues and/or organs during or after a surgical procedure. The composition is a flowable solution of a hydrophobically-modified chitosan, wherein the hydrophobic modifications are selected to allow for adherence to tissue, cohesiveness of the composition upon application to tissue, and degradation over about two weeks after application. A method for providing a barrier between tissues and/or organs during or after a surgical procedure. Applying a hydrophobically-modified polymer to surfaces of tissues or organs in within a surgical site either before, during, and/or after a surgical procedure, wherein the modified polymer reduces adhesion between organs or tissues after surgery.

14 Claims, 3 Drawing Sheets

(56) References Cited

U.S. PATENT DOCUMENTS

| | | | |
|---|---|---|---|
| 8,668,899 B2* | 3/2014 | Dowling | A61L 24/0026 424/94.6 |
| 11,274,194 B2* | 3/2022 | Dowling | A61K 31/717 |
| 11,298,517 B2* | 4/2022 | Dowling | A61L 26/0076 |
| 11,787,922 B2* | 10/2023 | Dowling | C08L 5/04 536/20 |
| 2002/0028181 A1 | 3/2002 | Miller et al. | |
| 2002/0042473 A1 | 4/2002 | Trollsas et al. | |
| 2002/0068151 A1 | 6/2002 | Kim et al. | |
| 2004/0001893 A1 | 1/2004 | Stupp et al. | |
| 2004/0214736 A1 | 10/2004 | Modi | |
| 2005/0038369 A1 | 2/2005 | Gregory et al. | |
| 2005/0147656 A1 | 7/2005 | McCarthy et al. | |
| 2005/0181027 A1 | 8/2005 | Messinger | |
| 2006/0094060 A1 | 5/2006 | Jarhede et al. | |
| 2006/0167116 A1 | 7/2006 | Uchegbu et al. | |
| 2006/0211973 A1 | 9/2006 | Gregory et al. | |
| 2006/0269485 A1 | 11/2006 | Friedman et al. | |
| 2007/0055364 A1 | 3/2007 | Hossainy et al. | |
| 2007/0148215 A1 | 6/2007 | Teslenko et al. | |
| 2008/0103228 A1 | 5/2008 | Falcone et al. | |
| 2008/0254104 A1 | 10/2008 | Raghavan et al. | |
| 2009/0062849 A1 | 3/2009 | Dowling | |
| 2009/0192429 A1 | 7/2009 | Daniels et al. | |
| 2009/0226391 A1 | 9/2009 | Roberts et al. | |
| 2010/0256671 A1 | 10/2010 | Falus | |
| 2011/0020258 A1 | 1/2011 | Lorant | |
| 2011/0052665 A1 | 3/2011 | Hardy et al. | |
| 2011/0217785 A1 | 9/2011 | Liu et al. | |
| 2011/0280857 A1 | 11/2011 | Dowling et al. | |
| 2012/0058970 A1 | 3/2012 | Dowling | |
| 2012/0252703 A1 | 10/2012 | Dowling | |
| 2013/0149385 A1 | 6/2013 | Mousa | |
| 2019/0159992 A1 | 5/2019 | Dowling | |

FOREIGN PATENT DOCUMENTS

| | | | | |
|---|---|---|---|---|
| FR | 2933297 A1 | 1/2010 | | |
| WO | 1999002122 A1 | 1/1999 | | |
| WO | WO-9903481 A1 * | 1/1999 | | A61K 31/715 |
| WO | WO-2018191705 A1 * | 10/2018 | | A61K 31/717 |

OTHER PUBLICATIONS

Kim, Seung-Ho MD; Stezoski, S. William; Safar, Peter MD; Capone, Antonio MD; Tisherman, Samuel MD. "Hypothermia and Minimal Fluid Resuscitation Increase Survival after Uncontrolled Hemorrhagic Shock in Rats" Journal of Trauma-Injury Infection & Critical Care. 42(2):213-222, Feb. 1997.

Kjoniksen et al., Light Scattering Study of Semidilute Aqueous Systems of Chitosan and Hydrophobically Modified Chitosans, Macromolecules 31(23):8142-8148 (1998).

Knoll, W.; Frank, C. W.; Heibel, C.; Naumann, R.; Offenhausser, A.; Ruhe, J.; Schmidt, E. K.; Shen, W. W.; Sinner, A. "Functional tethered lipid bilayers." J. Biotechnol. 2000, 74, 137-58.

Koehler et al., Microstructure and Dynamics of Wormlike Micellar Solutions Formed by Mixing Cationic and Anionic Surfactants, J. Phys. Chem. B 104(47):11035-11044 (2000).

Kozen, Buddy G et al., An Alternative Hemostatic Dressing: Comparison of CELOX, HemCon, and QuikClot, Acad. Emerg. Med. 15:74-81(2008).

Kubota et al. Gelation dynamics and gel structure of fibrinogen. Colloids Surf B Biointerfaces 38:103-109, 2004.

Kumar, R.; Raghavan, S. R. "Thermothickening in solutions of telechelic associating polymers and cyclodextrins." Langmuir 2010, 26, 56-62.

Kurth, Dirk G. and Thomas Bein. "Monomolecular Layers and Thin Films of Silane Coupling Agents by Vapor-Phase Adsorption on Oxidized Aluminum." J. Phys. Chem. 1992. 96. 6707-6712.

Larson, M. J.; Bowersox, J. C.; Lim, R. C.; Hess, J. R. "Efficacy of a fibrin hemostatic bandage in controlling hemorrhage from experimental arterial injuries." Arch. Surg. 1995, 130, 420-422.

Lee et al., Transition from Unilamellar to Bilamellar Vesicles Induced by an Amphiphilic Biopolymer, Phys. Review Letters, 96:048102-1-048102-4 (2006).

Lee et al., Vesicle-Biopolymer Gels: Networks of Surfactant Vesicles Connected by Associating Biopolymers, Langmuir 21(1):26-33 (2005).

Lew, W. K.; Weaver, F. A. "Clinical use of topical thrombin as a surgical hemostat." Biologics 2008, 2, 593-599.

Li et al., Multivesicular Liposomes for Oral Delivery of Recombinant Human Epidermal Growth Factor, Arch Pharm Res 28(8):988-994 (2005).

Lu, S. et al. "Preparation of Water-Soluble Chitosan" Journal of Applied Polymer Science 91, 3497-2503 (2004).

Lunelli et al., Covalently Anchored Lipid Structures on Amine-Enriched Polystyrene, Langmuir 21(18):8338-8343 (2005).

Macfarlane, R. G. "An enzyme cascade in the blood clotting mechanism, and its function as a biological amplifier." Nature 1964, 202, 498-499.

Malette, William G. et al. Chitosan: A New Hemostatic, The Annals of Thoracic Surgery 36(1):55-58 (1983).

Mansur Yalpani and Laurence D. Hall, Some Chemical and Analytical Aspects of Polysaccharide Modifications. Formation of Branched-Chain, Soluble Chitosan Derivatives, Macromolecules 17(3):272-281 (1984).

Mathivet et al., Shape Change and Physical Properties of Giant Phospholipid Vesicles Prepared in the Presence of an AC Electric Field, Biophysical Journal 70:1112-1121 (1996).

Meier, Wolfgang et al., Vesicle and Cell Networks: Interconnecting Cells by Synthetic Polymers, Langmuir 12:5028-5032 (1996).

Michael I. Fisher and Torbjorn Tjarnhage, Structure and Activity of Lipid Membrane Biosensor Surfaces Studied with Atomic Force Microscopy and a Resonant Mirror, Biosensors & Bioelectronics 15:463-471 (2000).

Muzzarelli, R et al., Antimicrobial Properties of N-Carboxybutyl Chtosan, Antimicrobial Agents and Chemotherapy, 34(10):2019-2023 (1990).

Naumann et al., Proton Transport Through a Peptide-tethered Pilayer Lipid Membrane by the H.+-.ATP Synthase from Chloroplasts Measured by Impedance Spectroscopy, Biosensors and Bioelectronics 17:25-34 (2002).

Naumann, C. A.; Prucker, O.; Lehmann, T.; Ruhe, J.; Knoll, W.; Frank, C. W. "The polymer-supported phospholipid bilayer: Tethering as a new approach to substrate-membrane stabilization." Biomacromolecules2002, 3, 27-35.

Neuffer, M. C.; McDivitt, J .; Rose, D.; King, K.; Cloonan, C. C.; Vayer, J. S. "Hemostatic dressings for the first responder: A review." Military Med. 2004, 169, 716-720.

New ! Pioneer Chip L1 Improved binding studies in model membrane systems, BIA Journal No. 2 1998.

Nikolelis et al., A Minisensor for the Rapid Screening of Sucralose Based on Surface-stabilized Bilayer Lipid Membranes, Biosensors & Bioelectronics 15:439-444 (2000).

Paul S. Cremer and Steven G. Boxer, Formation and Spreading of Lipid Bilayers on Planar Glass Supports, J. Phys. Chem. B 103(13):2554-2559 (1999).

Wu et al., Spatially Selective Deposition of a Reactive Polysaccharide Layer onto a Patterned Template, Langmuir 19 (3):519-524 (2003).

Pusateri, A. E.; Holcomb, J. B.; Kheirabadi, B. S.; Alam, H. B.; Wade, C. E.; Ryan, K. L. "Making sense of the preclinical literature on advanced hemostatic products." J. Trauma 2006, 60, 674-682.

Puu et al., Retained Activities of Some Membrane Proteins in Stable Lipid Bilayers on a Solid Support, Biosensors and Bioelectronics 10:463-476 (1995).

Whang, Hyun Suk et al., Hemostatic Agents Derived from Chitin and Chitosan, J. Macromolecular Science 45:309-323 (2005).

Raghavan, S. R.; Cipriano, B. H. Gel formation: Phase diagrams using tabletop rheology and calorimetry. InMolecular Gels; Weiss, R. G., Terech, P., Eds.; Springer: Dordrecht, 2005; pp. 233-244.

Rao, S. B.; Sharma, C. P. "Use of chitosan as a biomaterial: Studies on its safety and hemostatic potential." J. Biomed. Mater. Res. 1997, 34, 21-28.

(56) References Cited

OTHER PUBLICATIONS

Tonelli, A. E. "Nanostructuring and functionalizing polymers with cyclodextrins." Polymer 2008, 49, 1725-1736.
Reiss, R. F.; Oz, M. C. "Autologous fibrin glue: Production and clinical use." Transfusion Med. Rev. 1996, 10, 85-92.
Rodriguez, M.S., et al."Interaction between chitosan and oil under stomach and duodenal digestive chemical conditions" Biosci. Biotechnol. Biochem. 69 (11), 2057-2062 (2005).
Rongen et al., Liposomes and Immunoassays, J. Immunol. Methods 204:105-133 (1997).
Stavroula Sofou and James L. Thomas, Stable Adhesion of Phospholipid Vesicles to Modified Gold Surfaces, Biosensors and Bioelectronics 18:445-455 (2003).
Stewart, R. M.; Myers, J. G.; Dent, D. L.; Ermis, P.; Gray, G. A.; Villarreal, R.; Blow, O.; Woods, B.; McFarland, M.; Garavaglia, J.; Root, H. D.; Pruitt, B. A. "Seven hundred fifty-three consecutive deaths in a level 1 trauma center: The argument for injury prevention." J. Trauma 2003, 54, 66-70.
Tanaka, M.; Sackmann, E. "Polymer-supported membranes as models of the cell surface." Nature 2005,437, 656-663.
Szymanska et al., Fullerene Modified Supported Lipid Membrane as Sensitive Element of Sensor for Odorants, Biosensors & Bioelectronics 16:911-915 (2001).
Tanweer A. Khan and Kok Khiang Peh, A Preliminary Investigation of Chitosan Film as Dressing for Punch Biopsy Wound in Rats, J. Pharm. Pharmaceut. Sci. 6(1):20-26 (2003).
Tangpasuthadol, Surface Modification of Chitosan Films. Effects of Hydrophobicity on Protein Adsorption, Carbohydrate Res. 338:937-942 (2003).
Alam, Hasan B. et al., Comparative Analysis of Hemostatic Agents in a Swine Model of Lethal Groin Injury, J. Trauma 54:1077-1082 (2003).
Allerbo et al., Simulation of lipid vesicle rupture induced by an adjacent supported lipid bilayer patch (Colloids and Surfaces B: Biointerfaces 2011, 82, 632-636).
Anderluh et al., Properties of Nonfused Liposomes Immobilized on an L1 Biacore Chip and Their Permeabilization by a Eukaryotic Pore-forming Toxin, Anal. Biochem. 344:43-52 (2005).
Angelova, M. I.; Dimitrov, D. S. "Liposome electroformation." Faraday Discuss. 1986, 81, 303-306.
Ankit R. Patel and Curtis W. Frank, Quantitative Analysis of Tethered Vesicle Assemblies by Quartz Crystal Microbalance with Dissipation Monitoring: Binding Dynamics and Bound Water Content, Langmuir 22(18):7587-7599 (2006).
Arnaud, F.; Teranishi, K.; Tomori, T.; Carr, W.; McCarron, R. "Comparison of 10 hemostatic dressings in a groin puncture model in swine." J. Vascular Surg. 2009, 50, 632-639.
Kheirabadi, B. S.; Scherer, M. R.; Estep, J. S.; Dubick, M. A.; Holcomb, J. B. "Determination of Efficacy of New Hemostatic Dressings in a Model of Extremity Arterial Hemorrhage in Swine." J. Trauma 2009, 67, 450-460.
Bochicchio, G .; Kilbourne, M .; Kuehn, R .; Keledjian, K .; Hess, J .; Scalea, T. "Use of a modified chitosan dressing in a hypothermic coagulopathic grade V liver injury model." Am. J. Surg. 2009, 198, 617-622.
Boukobza et al., Immobilization in Surface-Tethered Lipid Vesicles as a New Tool for Single Biomolecule Spectroscopy, J. Phys. Chem. B 105(48):12165-12170 (2001).
Brandenberg, Greg et al., Chitosan: A New Topical Hemostatic Agent for Diffuse Capillary Bleeding in Brain Tissue, Neurosurgery 15(1): 9-13 (1984).
Burkatovskaya, Marina et al., Use of Chitosan Bandage to Prevent Fatal Infections Developing From Highly Contaminated Wounds in Mice, Biomaterials 27:4157-4164 (2006).
Champion, H. R.; Bellamy, R. F.; Roberts, C. P.; Leppaniemi, A. "A profile of combat injury." J. Trauma2003, 54, S13-S19.
Chenite, A. et al."Rheological characterization of thermogelling chitosan/glycerol-phosphate solutions" Carbohydrate Polymers 46, 39-47 (2001).

Chiaki Yoshina-Ishii and Steven G. Boxer, Arrays of Mobile Tethered Vesicles on Supported Lipid Bilayers, J. Am. Chem. Soc. 125(13):3696-3697 (2003).
Christensen, S. M.; Stamou, D. "Surface-based lipid vesicle reactor systems: fabrication and applications." Soft Matter 2007, 3, 828-836.
Cooper et al., A Vesicle Capture Sensor Chip for Kinetic Analysis of Interactions with Membrane-Bound Receptors, Anal. Biochem. 277:196-205 (2000).
Khan et al., Mechanical, Bioadhesive Strength and Biological Evaluations of Chitosan Films for Wound Dressing, J. Pharm. Pharmaceut. Sci. 3(3):303-311 (2000).
D. D. Lasic and D. Papahadjopoulos, Liposomes Revisited, Science 267(5202): 1275-1276 (1995).
Dan D. Lasic, Novel Applications of Liposomes, Trens in Biotechnology (TIBTECH) 16:307-321 (1998).
Deng, Y.; Wang, Y.; Holtz, B.; Li, J. Y.; Traaseth, N.; Veglia, G.; Stottrup, B. J.; Elde, R.; Pei, D. Q.; Guo, A.; Zhu, X. Y. "Fluidic and air-stable supported lipid bilayer and cell-mimicking microarrays." J. Am. Chem. Soc.2008, 130, 6267-6271.
Desbrieres et al., Hydrophobic Derivatives of Chitosan: Characterization and Rheological Behaviour, Biological Macromolecules, 19:21-28 (1996).
Dimitrievski et al., Influence of Lipid-Bilayer-Associated Molecules on Lipid-Vesicle Adsorption (Langmuir 2010, 26 (8), 5706-5714).
Dimitrievski et al., Simujlations of Lipid Vesicle Adsorption for Different Lipid mixtures (Langmuir 2008, 24, 4077-4091).
Doolittle, R. F. "Fibrinogen and fibrin." Annu. Rev. Biochem. 1984, 53, 195-229.
Dowling, M.B., et al. "A self-assembling hydrophobically modified chitosan capable of reversible hemostatic action." Biomaterials. May 2011 Vo. 31, pp. 3351-3357.
Durian, Douglas J., et al. "Making a frothy shampoo or beer." Physics Today. pp. 62-63. May 2010.
Kean, T .; Thanou, M. "Biodegradation, biodistribution and toxicity of chitosan." Adv. Drug Deliv. Rev. 2010,62, 3-11.
Ellis-Behnke, R. G.; Liang, Y. X.; You, S. W.; Tay, D. K. C.; Zhang, S. G.; So, K. F.; Schneider, G. E. "Nano neuro knitting: Peptide nanofiber scaffold for brain repair and axon regeneration with functional return of vision." Proc. Natl. Acad. Sci. U. S. A. 2006, 103, 5054-5059.
Ellis-Behnke, R. G.; Liang, Y.- X.; Tay, D. K. C.; Kau, P. W. F.; Schneider, G. E.; Zhang, S.; Wu, W.; So, K.-F. "Nano hemostat solution: Immediate hemostasis at the nanoscale." Nanomedicine 2006, 2, 207-215.
Esquenet et al., Structural and Rheological Properties of Hydrophobically Modified Polysaccharide Associative Networks, Langmuir 20(9):3583-3592 (2004).
F W Verheugt, M J van Eenige, J C Res, M L Simoons, P W Serruys, F Vermeer, D C van Hoogenhuyze, P J Remme, C de Zwaan, and F Baer. Bleeding complications of intracoronary fibrinolytic therapy in acute myocardial infarction. Assessment of risk in a randomised trial. Br. Heart F. 1985, 54:455-9.
Fu et al., Protein stability in controlled-release systems, Nature Biotechnology 18:24-25 (2000).
GlaxoSmithKline. Bactroban Ointment: Prescribing Information. Research Triangle Park, NC. May 2005. Downloaded from the world wide web on Jan. 17, 2013:.
Gregory F. Payne and Srinivasa R. Raghavan, Chitosan: a Soft Interconnect for Hierarchical Assembly of Nano-scale Components, Soft Matter 3:521-527 (2007).
Hirano and Noishiki, The Blood Compatibility of Chitosan and N-Acylchitosans, J. Biochem. Materials Res. 413-417 (1985).
Kauvar, D. S.; Lefering R.; Wade, C. E. "Impact of hemorrhage on trauma outcome: An overview of epidemiology, clinical presentations, and therapeutic considerations." J. Trauma 2006, 60, S3-S9.
Ho et al. "Preparation and characterization of RGD-immobilized chitosan scaffolds", Biomaterials 26 (2005) 3197-3206, published Oct. 14, 2004.
Kaler et al., Phase Behavior and Structures of Mixtures of Anionic and Cationic Surfactants, J. Phys. Chem. 96(16): 6698-6707 (1992).

(56) References Cited

OTHER PUBLICATIONS

Hong et al., Two-step Membrane Binding by Equinatoxin II, a Pore-forming Toxin from the Sea Anemone, Involves an Exposed Aromatic Cluster and a Flexible Helix, J. Biol. Chem. 277(44):41916-41924 (2002).

Hook et al., Supported Lipid Bilayers, Tethered Lipid Vesicles, and Vesicle Fusion Investigated Using Gravimetric, Plasmonic, and Microscopy Techniques, Biointerphases 3(2) (Jun. 2008).

Jung et al., Quantification of Tight Binding to Surface-Immobilized Phospholipid Vesicles Using Surface Plasmon Resonance: Binding Constant of Phospholipase A2, J. Am. Chem. Soc. 122(17):4177-4184 (2000).

* cited by examiner

SYSTEM AND METHOD TO REDUCE TISSUE ORORGAN ADHESION

CROSS-REFERENCE TO RELATED APPLICATIONS

This application claims priority from U.S. Provisional Application Ser. No. 62/814,265, filed on Mar. 5, 2019, and entitled "SYSTEM AND METHOD TO REDUCE POST-SURGICAL ORGAN ADHESION"; which is incorporated herein by reference on its entirety.

BACKGROUND

A common complication after surgical procedures is tissue adhesion. After parenchymal tissues are disturbed due to surgery, infections, trauma, radiation, or other outside influence, the body reacts by attempting to repair the damaged tissue. The repair of damaged tissue may be in the form of a thin film or thick fibers that form scars. In some instances, these tissue additions form between organs creating issues for the patient. In abdominal surgeries, the adhesions may result in bowel obstructions and cause pelvic pain.

There are three approved methods for prevention of post-surgical adhesions currently available under the commercial names of Adept®, Interceed®, and Seprafilm®. See González-Quintero and Cruz-Pachon, Preventing Adhesions in Obstetric and Gynecologic Surgical Procedures, Reviews in Obstetrics & Gynecology 2(1):38-45 (2009). Adept® is a 4% Icodextrin solution made of an α(1-4)-linked glucose polymer that acts via hydroflotation; but it has been shown to have limited efficacy. Interceed® is made of oxidized regenerated cellulose, formulated as sheets placed at the surgical site; but it appears to be ineffective in the presence of blood. Seprafilm® is chemically modified hyaluronic acid and carboxymethyl-cellulose and is delivered in the form of thin films. None of the existing methods of prevention of post-surgical adhesions are significantly effective in the presence of blood.

BRIEF SUMMARY OF THE INVENTION

In various aspects and embodiments, the invention provides compositions and methods for providing a barrier between tissues and/or organs during surgery and post-surgery. In various embodiments, the invention reduces or prevents tissue or organ scarring or adhesion. The invention relates to application of a hydrophobically-modified polymer to a surgical site that is at risk of tissue or organ adhesion as a result of a surgical procedure. The surgical site in some embodiments is not in need of hemostatic treatment. In various embodiments, the hydrophobically-modified polymer is designed to balance adhesion to tissue, cohesion of the composition including in the presence of high exudate, and degradation rate. In one embodiment, the modified polymer is amphiphilic, preferably hydrophobically-modified chitosan. In one embodiment, the hydrophobically-modified chitosan has a level of deacetylation of from about 40% to about 90%. In other embodiments, from about 1% to about 50% of functional groups are occupied by a hydrophobic group. In some embodiments, the modified polymer has about 5 to about 100 moles of hydrophobic group per mole of polymer. In other embodiments, the molecular weight of the polymer is from about 40,000 to about 500,000 Daltons.

The hydrophobically-modified polymer has hydrophobic groups selected from linear, branched, or cyclic hydrocarbon groups. In some embodiments, the hydrophobic groups comprise saturated hydrocarbons, which are optionally acyl groups. In other embodiments, the hydrophobic groups comprise unsaturated, aromatic, and/or polyaromatic hydrocarbons. In yet further embodiments, the hydrophobic groups each have from 1 to about 36 carbon atoms. In other embodiments, the hydrophobic groups are independently selected from linear hydrocarbons having from 1 to about 18 carbon atoms.

In some embodiments, the hydrophobically-modified polymer is applied as a flowable composition, including, as a foam, cream, or hydrogel, which can be applied to tissue or organ surfaces to act as a barrier (to reduce contact between these surfaces during or as a result of the surgical procedure). For example, the modified polymer may be an aqueous formulation and delivered from a container having at least two compartments each containing a releasable, flowable product; wherein a first compartment comprises a solution of a acidified hydrophobically-modified polymer that gels in the presence of blood, and a second compartment comprises a solution of a bicarbonate or carbonate salt at an alkaline pH and optionally a negatively-charged polymer. In one embodiment, the modified polymer is present at 0.1% to about 2% by weight of the solution in the first compartment. In some embodiments, the modified polymer is formulated at a pH of from 2.5 to 4.5. In other embodiments, the modified polymer is formulated with a weak organic acid, such as lactic acid, ascorbic acid, and/or citric acid. In some embodiments, the second compartment comprises a solution comprising sodium bicarbonate, preferably in a concentration of around 0.1 wt % to about 1 wt % or from about 0.2M to about 0.5M. In some embodiments, the bicarbonate or carbonate salt is formulated at pH 8 to 10. When the solutions are mixed upon application to a tissue or organ surface, production of $CO_2$ will result in a stable foam that adheres to the tissue surface and provides a barrier between such surfaces. The foam (or other flowable form of the composition) can be spread on the surfaces by the medical personnel to provide a suitable barrier between tissue and organ surfaces. The barrier is effective even in the presence of blood or high exudate.

In some embodiments, the second compartment contains a negatively charged polymer, such as alginate, pectin, dextran, carboxymethylcellulose, or xanthan gum. In some embodiments, the alginate is hydrophobically-modified. The container, in some embodiments, is a spray bottle, optionally with a propellant, or the container is a syringe. In some embodiments, releasing of the contents results in mixing of the releasable, flowable products within the syringe. In other embodiments, the flowable products results in production of $CO_2$, and foaming of the hydrophobically-modified polymer composition.

In one embodiment, the modified polymer has hydrophobic groups of at least two different sizes attached to the polymer backbone. Sizes can be selected to tune the degradation rate of the polymer, as well as cohesiveness of the composition and adhesion to tissues. In another embodiment, the polymer is chitosan, and hydrophobic groups are incorporated by anhydride chemistry. The polymer may have from 2 to about 10 different hydrophobic groups, and optionally from 2 to about 5 different hydrophobic groups. In some embodiments, the hydrophobic groups include at least one saturated hydrocarbon, which is optionally a conjugated fatty acid. The hydrophobic groups each have from 1 to about 100 carbon atoms.

The polymer may have at least one or two of (a) a C1 to C5 hydrocarbon group, which may be substituted; (b) a C6 to C12 hydrocarbon group, which may be substituted; (c) a C13 to C28 hydrocarbon group, which may be substituted; and (d) a hydrophobic group having a size greater than C28. In some preferred embodiments, the hydrophobic groups comprise a C1 to C4 hydrocarbon and a hydrocarbon greater than C6. In other embodiments, the C1 to C4 hydrocarbon group is present at 5:1 to 25:1 ratio with respect to hydrocarbon groups of C6 or greater. In other embodiments, the biopolymer has a hydrocarbon group of from C6 to C12 and a hydrocarbon group of from C16 or C18. In other embodiments, the hydrophobic groups comprise a C6 to C12 hydrocarbon and a C16 to C28 hydrocarbon. In yet further embodiments, the C6 to C12 hydrocarbons are present at a ratio of from 5:1 to 20:1 with respect to C16 to C28 hydrocarbons. The polymer may have hydrophobic modifications of C8 hydrocarbons and C14, C16, and/or C18 hydrocarbons. In other embodiments, the hydrophobic groups comprise a C1 to C4 hydrocarbon, a C6 to C12 hydrocarbon, and a C16 to C28 hydrocarbon. C1-4 hydrocarbon modifications in various embodiments will increase biodegradation properties of the material. Modifications higher than C16 provide benefits in cohesion of the composition, allowing the material to maintain integrity in the presence of blood or high exudate.

It is contemplated that the polymer may be formulated as a solid, liquid, gel, foam, or putty. In other embodiments, the polymer is lyophilized or is a dehydrated solution or dehydrated foam. In some embodiments, the modified polymer is present at 0.1% to about 5% by weight. In one embodiment, the polymer is formulated with at least one synthetic polymer, such as polyvinyl alcohol.

The method described herein can be used to treat a surgical site that is not bleeding or is not in need of hemostatic treatment. In a further embodiment, polymer degrades after application. In some embodiments, the polymer degrades within a defined period of time. The degradation occurs within a period of two months, one month, one week, or within two days, in some embodiments.

DESCRIPTION OF THE DRAWINGS

The invention described herein can be understood in view of the following drawings.

DETAILED DESCRIPTION OF THE INVENTION

Figure 1:
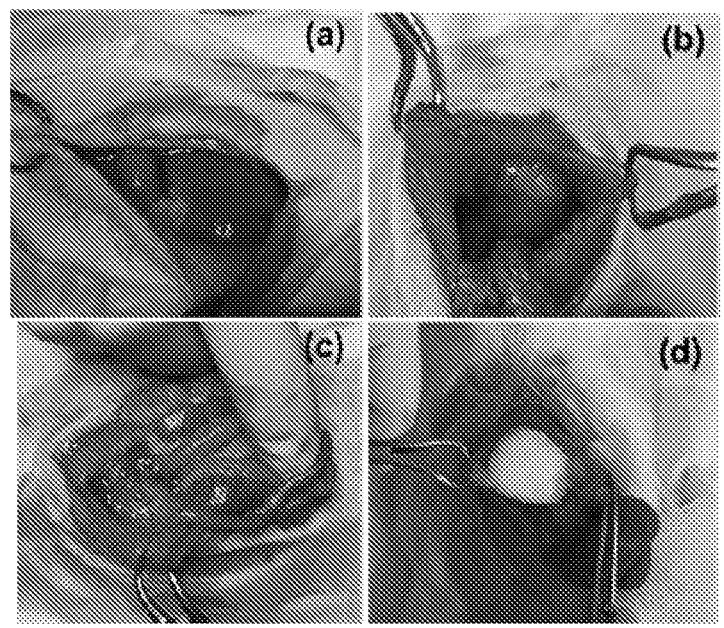
FIG. 1. Photographs of agents immediately post-treatment of hepatic injury. (a) no treatment control, (b) Tisseel® fibrin sealant (FS), (c) chitosan (CS), (d) hm-chitosan (HM-CS).

In various aspects and embodiments, the invention provides a composition and method for applying a barrier between tissues and organs prior to, during, or after a surgical procedure, to, for example, reduce tissue or organ damage and/or scarring, and/or to reduce or prevent formation of adhesions between organs and/or tissues as a result of the surgery. The compositions and methods involve application of a hydrophobically-modified polymer (hm-polymer) to parenchymal surfaces of tissues during surgery, e.g., tissues or organs that are at risk of adhesion formation. Specifically, the invention involves application of the composition to organ and/or tissue surfaces, including flowable compositions, over an entire area (or over substantially the entire area) that is at risk of adhesion formation as a result of the surgery.

In one embodiment, the composition for providing a barrier between tissues and/or organs during or after a surgical procedure, consists of a flowable solution of a hydrophobically-modified chitosan, wherein the hydrophobic modifications are selected to allow for adherence to tissue, cohesiveness of the composition upon application to tissue, and degradation after application. The composition is antibacterial in some embodiments. In other embodiments, the composition creates an antibacterial barrier when applied to a tissue. The composition creates an antibacterial barrier when applied to a surgical site in some embodiments.

In some embodiments, the surfaces are not in need of hemostatic treatment, in that there is no bleeding cut or bleeding wound on the surface. In one embodiment, the polymer is applied to a bleeding wound or to a wound that is not bleeding. In some embodiments, the composition is applied to surfaces at the start of surgery, thereby providing a barrier between tissues and organ surfaces, as well as providing hemostatic protection for small bleeds that may occur as a result of the procedure. In some embodiments, the composition is applied to surfaces at the conclusion of the procedure, before the surgical site is closed. The composition is allowed to remain with the subject, where it degrades over time. As disclosed herein, the modified polymer reduces adhesions between organs after surgery. In various embodiments, the composition is easy to handle and safe to apply as needed for prevention of tissue adhesion. It is contemplated that the method can be implemented in an animal subject or in a human subject.

An exemplary hm-polymer material is hm-chitosan (HM-CS). Chitosan (CS) is the common name of the linear, random copolymer that consists of β-(1-4)-linked D-glucosamine and N-acetyl-D-glucosamine. The molecular structure of chitosan consists of a linear backbone linked with glycosidic bonds. Chitosan is the major component of crustacean shells such as crab, shrimp, krill and crawfish shells. Additionally, chitosan is the second most abundant natural biopolymer after cellulose. Commercial chitosan samples are typically prepared by chemical de-N-acetylation of chitin under alkaline conditions. Depending on the source of the natural chitin (extracted from shells) and its production process, chitosan can differ in size (average molecular weight Mw) and degree of N-acetylation (% DA). While the poor solubility of chitosan in water and in common organic solvents restricts its applications, reactive amino groups in the chitosan backbone make it possible to chemically conjugate chitosan with various molecules and to modulate its properties for use surgical procedures.

The degree of deacetylation of chitin may range from about 40-100%, or in some embodiments, from 60 to 100%, which determines the charge density. In other embodiments, the level of deacetylation ranges from 40% to 90%, such as from 50% to 80%, or such as from 60% to 75%. In some embodiments the level of deacetylation is greater than 50%, or greater than 70%, or greater than 80%. The structure of chitosan (deacetylated), and is depicted in Formula 1:

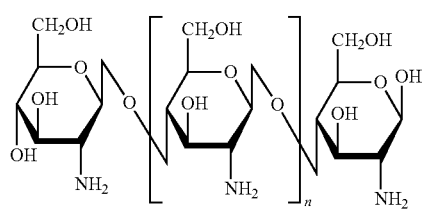

Formula 1

These repeating monomeric units include a free amino group, which makes molecules or compounds containing chitosan or its derivatives readily reactive. CS is a polysaccharide obtained from the exoskeleton of crab, shrimp, mollusks, and insects and is the second-most abundant biopolymer on earth next to cellulose. CS has long been of interest in wound treatment due to unique inherent qualities: (i) hemostatic effect, (ii) anti-microbial characteristics, (iii) scar-reduction, (iv) wound healing acceleration, and (v) durability. Due to these advantageous properties, several, CS-based products have been cleared by the FDA for external hemostatic applications for bleeding from minor cuts and scrapes to severe, life-threatening hemorrhage.

The hydrophobic modification of the chitosan backbone is through the association of an amphiphilic compound with the amino group, such that the hydrophobic tail of the amphiphilic compound is bound with the hydrophilic backbone structure. HM-CS amplifies the natural hemostatic capability of chitosan and, surprisingly, as described herein prevents post-surgical adhesions.

In some embodiments, the deacetylation leads to a degree of substitution of the hydrophobic substituent on the biopolymer (e.g., chitosan) that is from about 1 to about 100 moles of the hydrophobic substituent per mole of the biopolymer.

As used herein, the term "mol %" of a hydrophobic group refers to the % of available amines occupied by a hydrophobic group, assuming a level of deacetylation (e.g., in the case of chitosan) of 85%. In various embodiments, the level of hydrophobic modification allows for adhesion of the material to tissue surfaces. In some embodiments, the hm-chitosan has from 1 to about 50 mol % of hydrophobic groups, or in some embodiments, from 1 mol % to about 40 mol % of hydrophobic groups, or from about 1 mol % to about 20 mol % of hydrophobic groups, or from about 1 mol % to about 10 mol % of hydrophobic groups. In some embodiments, the hm-chitosan has from about 2 mol % to about 20 mol % of hydrophobic groups, or from about 5 mol % to about 20 mol % of hydrophobic groups The molecular weight of the polymer is from about 40,000 to about 500,000 Daltons.

In some embodiments, the molecular weight of the polymer is from about 25,000 to about 1,500,000 grams per mole. In various embodiments, the molecular weight of the biopolymer ranges from about 40,000 to about 500,000 grams per more, or from about 50,000 to about 250,000 grams per mole, or from about 50,000 to about 100,000 grams per mole. As used herein, the term "molecular weight" means weight average molecular weight. Methods for determining average molecular weight of biopolymers include low angle laser light scattering (LLS) and Size Exclusion Chromatography (SEC). In performing low angle LLS, a dilute solution of the polysaccharide, typically 2% or less, is placed in the path of a monochromatic laser. Light scattered from the sample hits the detector, which is positioned at a low angle relative to the laser source. Fluctuation in scattered light over time is correlated with the average molecular weight of the polysaccharide in solution. In performing SEC measurements, again a dilute solution of biopolymer, typically 2% or less, is injected into a packed column. The polysaccharide is separated based on the size of the dissolved polymer molecules and compared with a series of standards to derive the molecular weight.

Hydrophobic modifications of CS allow the biopolymer to be used in a solution format, an advantage over unmodified CS. CS-based external-use hemostats historically have all been solid, textile-based compression devices. In the solid state, CS acid salts adhere to bleeding sites due to the mucoadhesive properties of the biopolymer backbone. However, in solution, CS does not staunch blood flow, even though it electrostatically interacts with blood cells. In contrast, HM-CS allows for the formation of a 3-dimensional network with blood cells, thus forming a physical barrier able to control bleeding without compression. The hydrogelating characteristics of HM-CS results in the polymer acting more like a fibrin sealant in the presence of blood. Due to this unique property, HM-CS represents a useful platform to create fibrin sealant mimics which are ready-for-use at room temperature.

Known hydrophobically-modified polymers generally have one length of hydrophobic grafts to the backbone of the polymer, albeit at various grafting densities. Variable-length hydrophobes decorated along the hydrophilic polymer backbone allow for precise control over the behavior of the resulting amphiphilic polymer. Such control allows for enhanced functionality of the amphiphilic polymer relative to standard single-length hydrophobe grafting designs. The enhanced functionalities can result from novel three dimensional structures created by these polymers.

In various embodiments, hydrophobically-modified polymers or compositions thereof, are modified with hydrophobic groups of at least two different sizes attached to the polymer backbone. The use of variable size hydrophobic modifications assists in modulating degradation kinetics of the polymer and can result in formulations that assist in preventing adhesion after surgical treatments. Shorter grafts can be employed to tune degradation. Larger grafts can be utilized to regulate material cohesiveness. Variable-length hydrophobically-modified polymers are a new class of associating polymers. These polymers provide a greater level of control over how these polymers interact with themselves and with other entities in an aqueous or organic environment. This results in a new regime of functionality which is conducive to reducing or preventing adhesion of parenchymal surfaces of tissues and parenchymal tissues as a result of a surgical intervention.

In some embodiments, the polymer or composition is a modified polymer that is amphiphilic. In some embodiments, the polymer is based on a polysaccharide backbone, such as chitosan, alginate, cellulosics, pectins, gellan gums, xanthan gums, dextrans, and hyaluronic acids, among others. In some embodiments, the polymer is a synthetic polymer (i.e., non-natural), such as polyethylene glycol, poly-lactic acid, poly-glycolic acid, poly lactic co-glycolic acid, poly lactic co-glycolic acid, polymethylmethacrylate (polymethylmethacrylic acid), poly ε-caprolactone, polyurethane, silicone, among others.

The form of the modified polymers used may vary to include standard states, derivatives and other various formulations. For example, the hm-cellulosics may be formed from, without limitation, hydroxyethyl cellulose, hydroxypropyl cellulose, methyl cellulose, hydroxypropyl methyl cellulose, and/or hydroethyl methyl cellulose. HM-CS may be prepared from, without limitation, the following chitosan salts: chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof. Hm-alginates may be prepared from, without limitation, sodium alginate, potassium alginate, magnesium alginate, calcium alginate, and/or aluminum alginate. It is to be understood that various other forms of any of these natural polysaccharides that provide the proper functional capabilities may be employed without departing from the scope and spirit of the present invention.

In some embodiments, the polymeric component is a mixture of polysaccharides. For instance, the mixture may be of various different sub-classes of a single polymer class. Alternatively, the mixture may include two or more different classes of polymers, for instance a cellulosic and a chitosan, an alginate and a chitosan, and an alginate and a cellulosic.

The polymer may have from 2 to about 10 different hydrophobic groups, and optionally from 2 to about 5 different hydrophobic groups (e.g., 2, 3, or 4 different hydrophobic groups). The hydrophobic groups may be independently selected from linear, branched, or cyclic hydrocarbon groups. For example, the hydrophobic groups may include at least one saturated hydrocarbon, which is optionally an acyl group. In some embodiments, the hydrophobic groups include at least one unsaturated, aromatic, or polyaromatic hydrocarbon.

In various embodiments, the hydrophobic groups each have from 1 to about 100 carbon atoms, or from 1 to about 50 carbon atoms. In some embodiments, the hydrophobic groups each have from 1 to about 28 carbon atoms. As utilized herein C(N) refers to the number of carbon atoms. For example, C1 is a single carbon substituent and C2 is a two-carbon chain. In some embodiments, the polymer (e.g., chitosan) has at least one or at least two of:

(a) a C1 to C5 hydrocarbon group, which is optionally substituted by non-hydrocarbon moieties;
(b) a C6 to C12 hydrocarbon group, which is optionally substituted with non-hydrocarbon moieties;
(c) a C13 to C28 hydrocarbon group, which is optionally substituted with non-hydrocarbon moieties;
(d) a hydrophobic group having a size greater than C28, which is optionally substituted with non-hydrocarbon moieties. Non-hydrocarbon moieties include heteroatoms or groups comprising heteroatoms such as O, N, S, or halogen.

In some embodiments, the hydrophobic groups comprise C8 hydrocarbon groups, which are present along with at least one of C14, C16, or C18 hydrocarbon groups at a ratio of from 5:1 to 20:1, such as from 5:1 to 15:1, or about 10:1 in some embodiments (C8 to C14/C16/C18).

In some embodiments, the hydrophobic groups comprise C10 or C12 hydrocarbon groups, which are present along with at least one of C14, C16, or C18 hydrocarbon groups at a ratio of from 2:1 to 10:1, such as from 2:1 to 8:1, or about 5:1 in some embodiments (C10/C12 to C14/C16/C18).

In some embodiments, the hydrophobic groups comprise a C1 to C4 hydrocarbon and a C6 to C12 hydrocarbon. In some embodiments, the hydrophobic groups comprise a C6 to C12 hydrocarbon and a C16 to C28 hydrocarbon. In some embodiments, the hydrophobic groups comprise a C1 to C4 hydrocarbon, a C6 to C12 hydrocarbon, and a C16 to C28 hydrocarbon.

In some embodiments, the C1 to C4 hydrocarbon groups (e.g., C1) is present at 5:1 to 25:1 with respect to other larger hydrophobic grafts (e.g., C6 or greater). In some embodiments, C1 to C4 hydrocarbon groups are present at from about 5:1 to about 20:1, or about 5:1 to about 15:1, or about 5:1 to about 10:1 with regard to larger hydrophobic grafts (C6 or greater). In some embodiments, C1 to C4 hydrocarbon groups (e.g., C1) is incorporated into the polymer along with C6 to C12 (e.g., C8 or C10 or C12), and C13 to C28 hydrocarbon groups (e.g., C16 or C18).

The polymer composition may be formulated as a solid, liquid, gel, foam, or putty. In some embodiments, the composition is flowable, and can be easily applied and spread onto tissue surfaces prior, during, and/or after a surgical procedure. In some embodiments, the polymer may be a solid, such as a thin film that can cover surfaces at risk of adhesion formation. In other embodiments, the polymer is formulated with one or more solvents. The solvents may comprise water. In some embodiments, the solvent comprises a biocompatible suitable solvent.

In some embodiments, the modified polymer is present at 0.1 to about 5% by weight in the composition, or in some embodiments, from 0.5 to 2.0% (e.g., about 0.5%, about 1.0%, 1.5%, or about 2%). In some embodiments, the polymer is formulated in conjunction with at least one synthetic polymer that is suitable for use in surgical procedures. Exemplary synthetic polymers include polythene, polystyrene, polyacrylate, polyamide, polyester, polyurethane, polysulfide, and polycarbonate.

In some embodiments, the modified polymer is applied to surfaces around the surgical site (e.g., parenchymal tissues) providing a barrier between these tissues or organs surrounding the wound. There are a myriad of material characteristics that are desired for a well-functioning modified polymer, including: (1) the material should be easy to apply (ideally flowable to conform to surfaces, cavities, and/or small areas), (2) the material should adhere to tissues to avoid the need for repeat or frequent application during the procedure (3) retain its mechanical integrity in the face of blood flow or exudate and (4) be safely bioresorbable if left inside the body after application. Traditionally, these attributes are evaluated by mixing a number of different components together (e.g. polymer, nanoparticles, and proteins), due to the assumption that a single material cannot provide all critical characteristics. While a single material that provides tunability in each of these categories would be ideal, such a material is difficult to design, because often chemistries which result in a favorable attribute in one area (e.g. adhesion), result in the detuning of attributes in another area (e.g. cohesion). Here, we describe a framework, utilizing the available chemistry along the chitosan backbone via free amine groups (for example) to create specific hydrophobic designs that employ multiple different grafting lengths and density of hydrophobic groups to achieve optimized properties in flowability, tissue adhesion, cohesion, biodegradation, and removability.

Hydrocarbons that find use in accordance with this disclosure may be classified as saturated hydrocarbons, unsaturated hydrocarbons, and aromatic hydrocarbons. From this basic classification system there exist many derivatives and further types of compounds that build therefrom. For example, numerous and varied compounds include more than one aromatic ring and are generally referred to as polyaromatic hydrocarbons (PAH). In some embodiments, the hydrophobic moiety is aliphatic. Aliphatic compounds, carbon atoms can be joined together in straight chains, branched chains, or rings (in which case they are called alicyclic). They can be joined by single bonds (alkanes), double bonds (alkenes), or triple bonds (alkynes). Besides hydrogen, other elements can be bound to the carbon chain, the most common being oxygen, nitrogen, sulfur, and chlorine. Those of ordinary skill in the art will recognize that other molecules may also be bound to the carbon chains and that compounds of such heteroatomic structure are contemplated as falling within the scope of the current invention.

The hydrophobic tail group of the amphiphilic compound bound to the polymer backbone of the current invention is capable of branching and/or allowing the inclusion of side chains onto its carbon backbone. It may be understood that the strength of the hydrophobic interaction is based upon the available amount of "hydrophobes" that may interact amongst themselves or one another. Thus, it may further promote the hydrophobic effect by increasing the amount of and/or hydrophobic nature of the hydrophobic tail group that is interacting. For instance, a hydrophobic tail group, which in its original form may include a hydrocarbon chain, may promote an increase in its hydrophobicity (ability to hydrophobically bond and strength of hydrophobic interaction) by having a hydrophobic side chain attach to one of the carbons of its carbon backbone.

The side chains may be linear chains, aromatic, aliphatic, cyclic, polycyclic, or any various other types of hydrophobic side chains as contemplated by those skilled in the art. Alicyclic Compound/Cycloalkane/Cycloalkene: an organic compound that is both aliphatic and cyclic with or without side chains attached; typically include one or more all-carbon rings (may be saturated or unsaturated), but no aromatic character. Aromatic hydrocarbon/Polycyclic aromatic hydrocarbon/Heterocyclic compound: organic compounds with a ring structure containing atoms in addition to carbon, such as nitrogen, oxygen, sulfur, chloride, as part of the ring; may be simple aromatic rings or non-aromatic rings. Some examples are pyridine ($C_5H_5N$), Pyrimidine ($C_4H_4N_2$) and Dioxane.

In some embodiments, the modified polymer (e.g., chitosan or other polymer disclosed herein) has both C8 and C18 acyl groups covalently attached to the backbone of the polymer, which is both adhesive to tissues, due to the C8 groups, and also cohesive under exudate flow, due the C18 groups, but prevents adhesion between tissues separated by the polymer. The C8 groups are fluid at room and body temperature, allowing the polymer to spread onto the cell surfaces more effectively, whereas the C18's on neighboring polymer chains hold the polymer molecules together strongly even in the presence of high exudate or blood flow. These embodiments can thus balance adhesive and cohesive properties. Traditional CS dressings fail due to either lack of adherence to tissue or lack of coherence once an initial seal has been achieved. More specifically, native chitosan is particularly good at adhering to wet, bleeding tissue.

In accordance with some embodiments, certain hydrophobes provide advantages for optimizing adherence (e.g., to the tissue site), and other hydrophobes are more advantageous for improving composition cohesion. In some embodiments, the material will produce an artificial clot upon exposure to blood. As used herein, the term "artificial clot" refers to physical networks of hydrophobically-modified polymers, blood cells, and surrounding tissue cells which effectively act as a solid barrier to prevent further blood loss. In the range of C6-C12 lengths, the hydrophobic grafts are useful in improving adhesion of the dressings to tissues but reduce adhesion between different tissues separated by the grafts. In the range of C13-C22 lengths, the hydrophobic grafts are useful in improving the cohesion of the dressings. By mixing hydrophobic grafts, for example, C12 and C18 attached to a composition has improved characteristics as compared to native chitosan, 5% C12 chitosan only, or 1% C18 chitosan only. In some embodiments, the polymer has from 1 mol % to 20 mol % C12 hydrophobic groups, or from 2 mol % to about 10 mol % C12 hydrophobic groups, or about 5 mol % C12 hydrophobic groups. In some embodiments, the polymer has from 0.5 mol % to 5 mol % C18 hydrophobic groups, such as from 0.5 mol % to 2 mol % (e.g., about 1 mol %) C18 hydrophobic groups. These may be present for example on medium molecular weight chitosan (MW-250 kDa).

For example, in some embodiments, the polymer is a syringeable gel. The C12 component allows for robust attachment of the gel to the mucosal surface, whereas the C18 component allows for cohesive matrix properties.

In some embodiments, the polymer is a thin film or powder that can be applied to surfaces around a surgical site. The dressing not only adheres strongly to the bleeding tissue (relative to native chitosan), but also holds together in the presence of significant blood pressure or exudate. While a single-length 5 mol % C12 adheres significantly more than native chitosan to wet tissue, it fails upon application of blood pressures much greater than 100 mmHg. In some embodiments, the polymer is a foam, including a sprayable foam created by mixing the HM-CS solution with liquefied gas under pressure in a canister. Upon opening the canister valve to atmospheric pressure, the gas causes rapidly expulsion of the HM-CS from the canister. The C12 component of the formulation allows for large expansion of the foam relative to the initial gel volume, whereas the C18 component allows for a mechanically integral final foam product. The foam described herein may also be a syringeable foam, where a double-barrel syringe system connected to a mixing tip is utilized. Gas is released upon mixing the material in one barrel, HM-CS dissolved in dilute organic acid (e.g., acetic acid) in water, with the material in the other barrel, a neutrally or negatively charged polymer dissolved in water containing a low concentration of sodium bicarbonate. Upon mixing with the acetic acid, the bicarbonate released carbon dioxide gas, causing the foaming and expansion of the HM-CS.

In some embodiments, the composition is a hydrogel, including a syringeable hydrogel that can be easily applied and spread to the required surfaces prior to, during, and/or after a surgical procedure. The material can be easily reapplied as necessary during the procedure. The hm-polymer in the gel composition (which may be in the range of 0.1 to 5 wt %) will adhere to the surfaces and provide the necessary barrier between the surfaces. The composition need not be physically removed.

In these embodiments, incorporation of small hydrophobic groups, such as C1 to C4 acyl chains, allows the chitosan to degrade more predictably from lysozyme activity in the body. This allows the material to be left inside the body after the procedure. More specifically, hydrophobic groups below the length of C6 do not substantially contribute towards material cohesion. However, hydrophobic modification in the range of C1 to C6 allow for a framework to optimize the degradation of the material inside the body via lysozymes. Particularly in the case of surgical use, it is ideal for the biomaterial to degrade quickly after the risk of adhesion formation has passed. For example, 5 mol % C12 and 30 mol % C1 attached to a medium molecular weight chitosan (MW-250 kDa) creates a composition having improved biodegradation characteristics relative to either native chitosan, 5 mol % C12 chitosan only, or 30 mol % C1 chitosan only. Other variations, including with C6 to C12 (e.g., C8 or C10 or C12) and C13 to C28 (e.g., C16 or C18) hydrocarbon groups are described herein. In some embodiments, C1 to C4 acyl chains are incorporated at from 10 mol % to 80 mol %, such as from 10 mol % to 60 mol %. In some embodiments, the C1 to C4 acyl chains are incorporated at 20 mol % to 60 mol %, or from 20 mol % to 50 mol %, or from 20 mol % to 40 mol %.

In some aspects, the invention provides a method for treating a surgical site after surgery by applying the polymer or composition to the surgical site, wherein the polymer or composition results in reduced formation of adhesions. In some embodiments, the surgical site is not in need of application of a hemostat or a hemostatic device, that is, the application sites do not involve a bleed. In some embodiments, the polymer degrades in the body within a defined period of time. In one embodiment, the polymer degrades after two days. The polymer degrades within about two months, within about one month, or within about two weeks, or within about one week, or within about two days. In some embodiments, the material is mechanically removable from the site without damaging the underlying tissue. In various embodiments, the modified polymer (in the amount employed) is soluble in aqueous environment.

In some embodiments, the composition has antimicrobial properties. While the mechanism of action of chitosan as an anti-microbial is a not well understood, two key contributing mechanisms likely play a role: (1) penetration into the bacterial cells and intercalation with plasmid DNA, thus preventing replication, and (2) physical immobilization of cells due to physical binding of bacteria into a robust cohesive network. Smaller hydrophobes (e.g., C1-C12) assist with interfacing with the cell membrane and/or cell wall, and larger hydrophobes (e.g., C13-C22) may assist with physical binding of the bacteria into immobilized networks. Hence, the variable-length design framework, along a wide span of polymer (e.g., chitosan) backbone lengths, allows for the creation of many unique molecules which can amplify a given mechanism towards bacterial death depending upon the clinical circumstances. Certain bacteria are more susceptible to penetration through the cell well (typically gram negative); infections caused robust bacteria may be limited to treatment via molecules that work only by physical bacteriostasis (e.g. multi-drug resistant bacteria).

In some embodiments, the polymer composition is a second-order (2nd Order), third-order (3rd Order) or fourth-order (4th Order) hm-polymer, such as a HM-CS. Further, the 2nd Order, 3rd Order, or 4th Order biopolymer can be based on a low molecular weight polymer (e.g., 50-200 kDa), a medium molecular weight biopolymer (200-400 kDa), or high molecular weight polymer (400 to 1,500 kDa).

In some embodiments, an aqueous solution for used in the method described herein can be based on a solution of the hm-biopolymer that is 0.1% to 5.0% by weight relative to the total weight of the composition, or in some embodiments, 0.5% to 4.0%, or 0.5% to 3.0% of the total weight of the composition, or 0.5% to 2.0% of the total weight of the composition. In some embodiments, the biopolymer is 1.0% to 5.0% by weight relative to the total weight of the composition of the biopolymer, or in some embodiments, 1.5% to 5.0%, or 2.0% to about 4.0% of the total weight of the composition.

In some aspects, the invention provides a composition for treatment of surgical sites to prevent or reduce formation of adhesions, and/or to reduce tissue or organ damage such as scarring. The composition comprise a flowable HM-chitosan composition that adheres to tissue surfaces, is cohesive in the presence of fluids (exudate), and biodegradable within about two months, within about one month, or within about two weeks, or within about one week, or within about two days. In one embodiment, the composition is a system that comprises a double barrel syringe chamber, where one chamber contains HM-CS solution in a dilute organic acid and the other chamber is filled with a foaming agent (e.g., bicarbonate) as described.

In some embodiments, the container is any container that allows for controlled release of the contents, such as a syringe. In some embodiments, the product comprises a double-barrel syringe comprising two compartments and a static mixing tip. The static mixing tip stabilizes carbon dioxide ($CO_2$) gas and allows for direct application of a hydrophobically-modified polymer foam.

The first compartment of the container contains a modified polymer, such as hydrophobically-modified chitosan. In some embodiments, the modified polymer is modified with C8 to C20 hydrophobic grafts (which can be linear hydrocarbon grafts present along the backbone of the polymer. In the case of hydrophobically-modified chitosan, about 10% to about 50% of available functional groups along the backbone may be occupied by the hydrophobic grafts. In some embodiments, the HM-CS includes C12 grafts as well as some grafts larger than C12 to provide added integrity to the foam. In some embodiments, from 5% to about 40% of the grafts are C16 or C18. In some embodiments, the modified polymer (e.g., HM-CS) may be present in the first container at about 0.1 to about 2% by weight of the solution in the first compartment, such as from 0.2 to 0.8% by weight in some embodiments. The modified polymer may be formulated at a pH of from 2.5 to 4.5, and in some embodiments from pH 3 to pH 4.5. In some embodiments, the modified polymer is dissolved in acetic acid, lactic acid, ascorbic acid, or citric acid. For example, in the case of acetic acid and HM-CS, the acetic acid may be from 0.3 to 0.5M.

The second compartment of the container comprises a solution of a carbonate or bicarbonate salt, such as sodium bicarbonate. In some embodiments, the bicarbonate solution is from 0.2 to 0.5M. The bicarbonate or carbonate solution may be at pH 8 to 10, or from about pH 8 to about pH 9. In some embodiments, second compartment further comprises one or more negatively charged polymers, which in some embodiments are hydrophobically-modified (e.g., hydrophobically-modified alginate).

Upon mixing of the first compartment and the second compartment using the mixing tip, an expanding foam is generated due to stabilization of bubbles formed from the generation of $CO_2$ gas. In various embodiments, the foam is stable for at least 10 minutes, is stable when mixed with blood, and allows for transfer of gases in some embodiments.

The foaming agent may be selected from solution of carbonate or bicarbonate salts, such as sodium bicarbonate. In some embodiments, the bicarbonate solution is from 0.2 to 0.5M. The bicarbonate or carbonate solution may be at pH 8 to 10, or from about pH 8 to about pH 9. In some alternative embodiments, the foaming agent compartment may include one or more negatively charged polymers, which in some embodiments are hydrophobically-modified.

In one embodiment, the system comprises a double barrel syringe chamber was capped to prevent leakage of fluid. 2 mL of polymer solution, either CS or HM-CS, at 2.0 wt % was added to one chamber of a double barrel syringe and the other chamber was filled with 2 mL of sodium bicarbonate solution. In another embodiment, the composition is a hydrogel, which may be syringeable.

One embodiment provides a method for treating parenchymal surfaces of tissues in animals and humans, which reduces inter-organ adhesion. The method of treatment includes the application of a hydrophobically-modified polymer to a tissue around a surgical site, which allows the wound to heal with reduced adhesion between separate organs or tissues in the area of the wound. In some embodiments, there is no adhesion between organs to which the composition is applied. In other embodiments, minimal adhesion is observed. As such, tissue separator is provided. The tissue separator is a composition of matter that prevents adhesion between different tissues or organs within a surgical site, namely, in the vicinity of the surgical site.

During surgery, there is a risk of tissue adhesion between damaged tissues at a wound site. This risk is due to the body's healing mechanisms. The method described here provides a polymer composition that can be used during surgery to reduce the risk of tissue adhesion between various tissues at a surgical site. In some embodiments, the tissue separator may also be a hemostat that assists in controlling bleeding that may occur during the procedure. In other embodiments, the surgical site does not comprise a bleed, that is, the surgical site is not in need of application of a hemostat.

As described herein, animal studies show that the method described herein results in reduced adhesion between tissues after application of the hydrophobically-modified polymer. Visual observation also demonstrated that only residual material remained within the abdominal cavity after application of hydrophobically-modified polymer to a surgical site. In some embodiments, the composition is applied to tissues and/or organs at locations that are not in need of treatment with a hemostat, that is, are not actively bleeding or injured.

In one embodiment, HM-CS is delivered as an injectable foam, which expands due to the creation of $CO_2$ gas upon mixing with sodium bicarbonate in the tip of a double-barrel syringe. As shown in the example below, the material is applied on a non-lethal liver excision in rats for characterizing properties following 1 and 6 weeks of exposure. HM-CS was compared to native CS, formulated in the same double-barrel syringe configuration, and a commercial FS gel product for effects on survival, morbidity/mortality, visual degradation of product and a microscopic analysis of the injury site. HM-CS used as a hemostatic wound treatment with internal biocompatibility in a rodent model of hepatic injury, evaluated alongside unmodified CS and FS control treatments after partial hepatectomy, wherein HM-CS successfully induce a stable clot with minimal inflammation and adhesions between organs observed in the lesion cavity six weeks post-application. FIG. 1 shows hemostatic agents immediately post-treatment of hepatic injury. (a) no treatment control, (b) Tisseel® fibrin sealant (FS), (c) chitosan (CS), (d) hm-chitosan (HM-CS).

This histological observation of no impairment of healing in HM-CS treated animals is encouraging, considering that previous studies have demonstrated CS-based dressings to result in significant capsular formation around the material. However, in these cases, solid chitosan dressings applied to an internal hemorrhage resulted in significantly more dry weight of the applied material relative to the dry weight of the "foaming gels" utilized in this application. When lysozymes infiltrate a solid polysaccharide network, held tightly together by a hydrogen-bonded crystal structure, the degradation profile is much more protracted, resulting in much greater risk of inflammation or capsule formation as fibroblasts and macrophages gather around the implant. In contrast, applying the polysaccharide in gel format allows for easier access of these critical enzymes to cleave the $\beta 1 \rightarrow 4$ linkages along the chitosan backbone without significant steric hindrance.

CS has been reported to bind fat inside the body, likely the reason for our observed residual material in deposits around the treatment site. The longer-term (>6 weeks) effect of fatty deposits on this material site is unknown, but this deposition is unlikely to cause significant risk to the treated subject, as the amount of fat deposited is quite small relative to the fat deposits in the rest of the body and did not enhance adhesion to other organs in the immediate vicinity of the lesion site. Also, the withholding of fat in these regions posed no significant increased morbidity or mortality.

Fibrin clots are known to degrade inside the body within 3-4 days. The results of the current study provide indirect evidence that both CS and HM-CS in a 2 wt % solution format, can degrade in approximately the same timeframe as fibrin. This fast-degradation observed relative to previously reported internal pre-clinical work with chitosan dressings is likely due to the steric availability of the chitosan backbone in a solubilized gel format. Adhesions in Tisseel®-treated animals are not surprising, given similar observations reported in several other studies. These adhesions were particularly significant at the six-week time point and considerably enhanced binding to other organs in the peritoneal cavity of FS-treated rodents.

The observation of faster biodegradation of HM-CS relative to CS has been observed previously. However, in these previous reports, the hydrophobic modification occurs simply through grafting of single carbon groups to the chitosan backbone through the reacetylation process. In Huang et al., chitosan with a significant portion of monosaccharide units along the backbone modified with N-acetyl groups appears to increase the speed to degradation relative to highly deacetylated, or highly acetylated chitin variants. It is important to note that above 50% acetylation of chitosan, the molecule becomes water insoluble, and thus intractable as a flowable agent. In the case of HM-CS, significant reacetylation relative to the CS molecule occurs, however the reacetylation in this case results in the grafting of hydrocarbon groups rather than the traditional methyl group introduced by standard reacetylation with acetic anhydride. Hydrophobic modification of chitosan with significantly larger sized hydrophobic grafts is likely to result in not only improved hemostatic effect, but also faster degradation of the molecule due to an increased relative ability of lysozymes to degrade the polymer.

In the example of one embodiment, the excision of medial lobe was not lethal, but represented a significant injury which could negatively impact both tissue necropsy and histopathology analyses. The selected injury type proved internal safety via survival study ensuring that the untreated controls remain alive. The reproducible injury allows the method to retain relevance towards ultimate clinical utility. The use of such a wound shows the applicability of the results to clinical utility as an internal agent for biosurgery. Thus, we selected a mild-to-moderate injury type did not result in death of the untreated controls, providing an excellent reproducible model.

Samples of HM-CS foam, CS foam and FS were applied to a non-lethal liver excision in rats and left inside the abdominal cavity to degrade over time. None of the materials used in this study resulted in signs of morbidity or mortality at either the 1-week or 6-week timepoints. Residual FS was evident at 6 weeks post-application in the form of significant adhesions observed between the hepatic injury site and surrounding tissues. In contrast, minimal adhesions were observed in CS and HM-CS animals. The explanted injury sites that were subjected to histopathological assessments demonstrated a comparable pattern of degradation and wound healing for the three test materials. This is the first survival study demonstrating safety and resorption of HM-CS.

Figure 2:
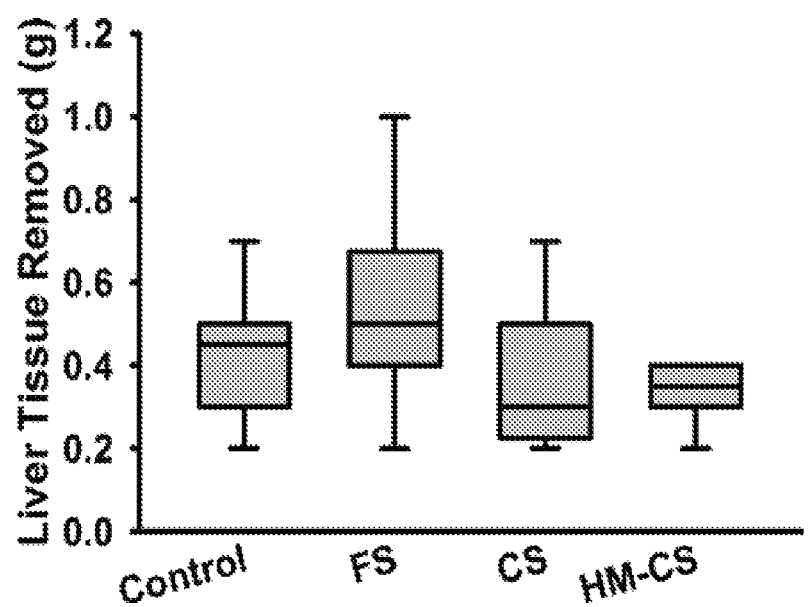
FIG. 2. Rodent liver excision weights per agent test group. In this rodent model of hepatic injury, each excised portion of liver lobe was weighed immediately following excision. Means are displayed, with error bars representing standard error (n=8 per group).
Figure 3:
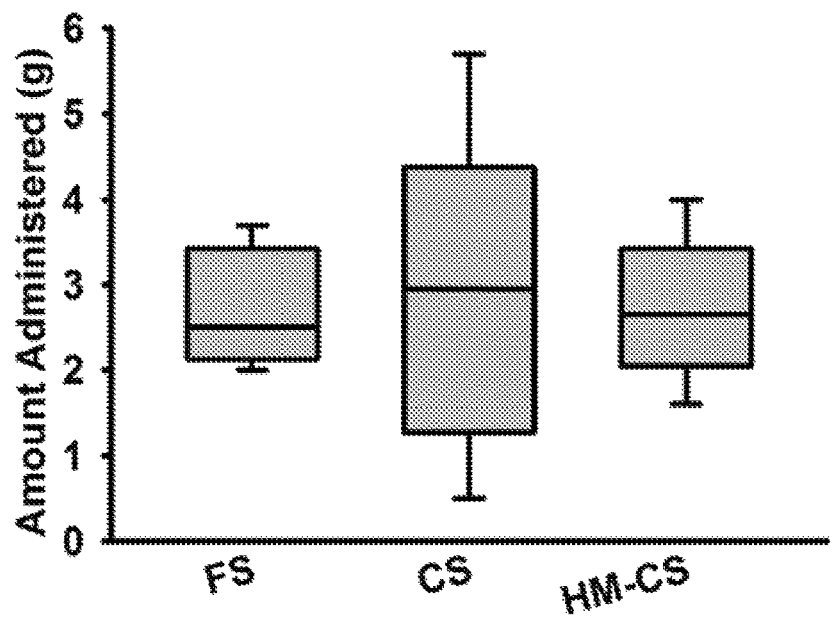
FIG. 3. Amount of agent delivered per test group. Exactly one minute after the excised liver lobe was removed, the agent was applied to the injury site and left on the injury for one hour to induce a stable clot. The entire volume of the pre-packaged syringes of agent were delivered, and difference in syringe mass was determined. Mean weights are displayed, with error bars representing standard error (n=8 per group).

There was no significant difference in amount of liver excised from rats between treatment groups. In FIG. 2, the average amount of liver removed per test group is shown. Cumulatively, an average of 0.4±0.3 g of liver was excised from the medial lobe of each rat. The standard deviation was high due to the small mass of liver that could be excised taken relative to the whole liver, in order to ensure non-lethality of the injury. Despite this variability, the average weights per test group was consistent (0.45 g No Treatment Control, 0.49 g FS, 0.31 g CS, 0.39 g HM-CS; P>0.05). Furthermore, as shown in FIG. 3, consistent amounts of test material were applied to the injury (2.4 g FS, 2.7 g CS, 2.5 g HM-CS; P>0.05), thus creating a relatively reliable framework to control for the amount of lobe excised relative to amount of hemostatic agent added.

Figure 4:
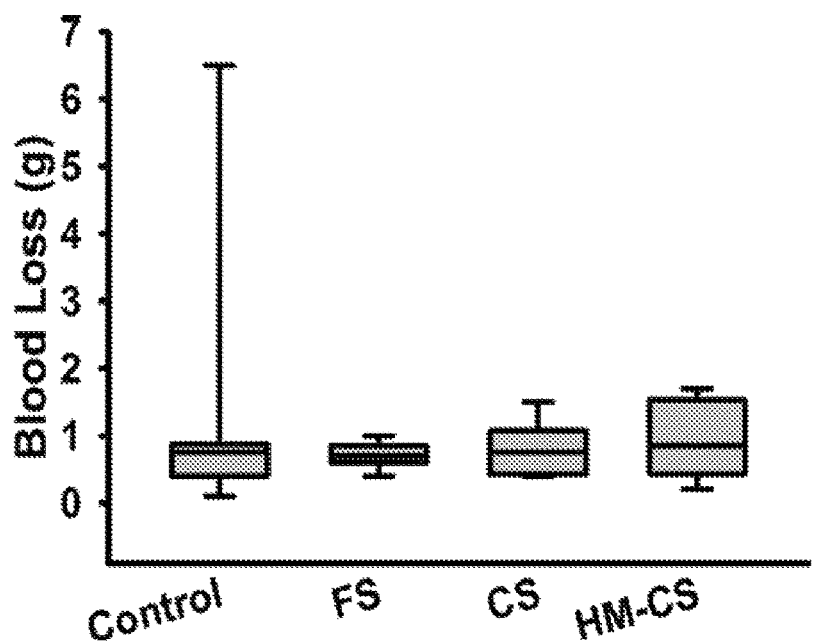
FIG. 4. Total blood loss per test group following hepatic injury. Blood loss was measured by weighing pre-weighed blood-soaked gauze pads immediately after the animal was closed. One control animal appeared to be coagulopathic and lost a significant amount more blood than any other animals in the study, but eventually the bleeding stopped and he did not die nor display any other abnormal symptoms during the six-week time period following the injury. Means are displayed, with error bars representing standard error (n=8 per group).

Bleeding after hepatic injury ceased within minutes of application of either HM-CS, CS, or FS treatments. Bleeding was observed for up to 30 minutes following injury in the control animals, before slowing and stopping to form a stable clot. There were no significant differences observed in amount of blood lost between animals among different treatment groups. FIG. 4 shows that the amount of blood loss is consistent between test groups, with approximately 1 g of blood collected in the 60 seconds prior to application of the given hemostatic agent.

All animals in the present example survived the hepatic injury and hemostat agent administration for the entire six-week time period post-injury regardless of hemostatic agent in the body cavity (P>0.05). Furthermore, none of the animals showed signs of morbidity or mortality in either the one-week group or the six-week group.

In the cases of FS and HM-CS, no impaired healing was apparent. For CS, histology showed possible impaired healing due to significant space in the interstices of infiltration fibroblast cells.

Figure 5:
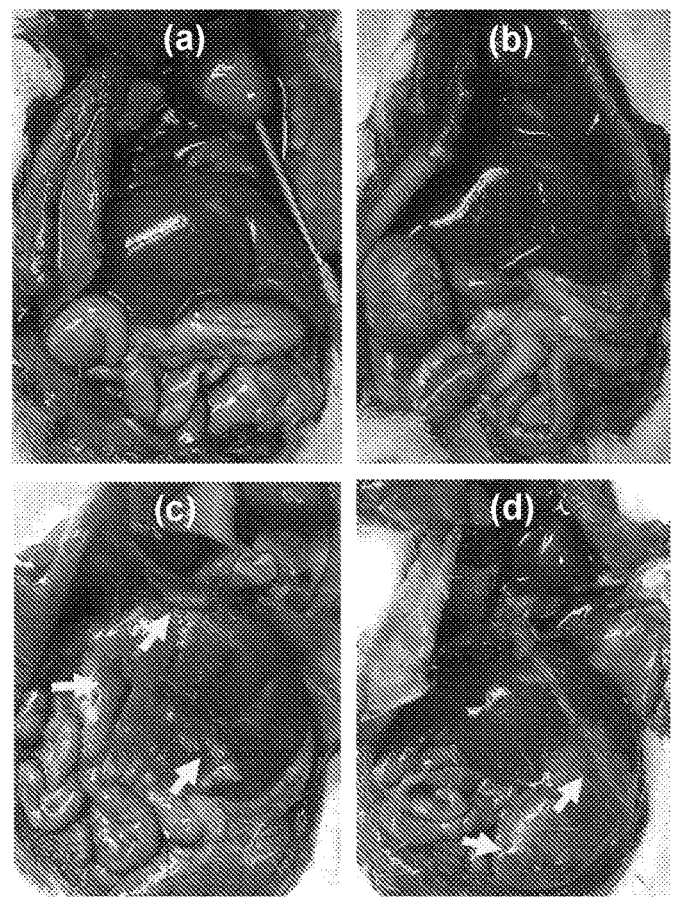
FIG. 5. Abdominal necropsy 6 weeks post-surgery for each agent. In (a), negative control shows normal healed lesion, no fat deposits on the liver, no discoloration. In (b), Tisseel® treatment shows normal appearing lesion area. In (c), CS treatment demonstrates small amounts of CS left in cavity, multiple fatty deposits around lesion area; yellow arrows point to fatty deposits. In (d), HM-CS treatment shows residual amounts of HM Chitosan left in the cavity around lesion and small fat deposits on intestines below; the arrow point to fatty deposits.

Visual observation demonstrated the only residual material remained within the abdominal cavity at the one-week time point for HM-CS, CS and FS. For the HM-CS and CS there appeared to be fatty deposits at the site of injury. FIG. 5 shows post-mortem livers prior to explanation. Negative controls showed a clean tissue presentation, except for some noticeable scarring at the injury site. FS treated wounds showed no visual residual material. Both CS and HM-CS showed fatty deposits around the injury site, likely due to interaction with the material during the early stages of clot formation after application.

At both one-week and six-week time points, the FS animals had significant (scores of 2.67±0.52 and 2.50±0.55, respectively) thick adhesions between the liver and colon. In contrast to FS, both CS and HM-CS produced filmy adhesions at one-week or six-weeks (adhesion scores of <2). HM-CS was nearly adhesion-free in all six of the animals in this test group at the six-week time-point with an average score of 0.33±0.52 (p<0.05 relative to FS group).

Figure 6:
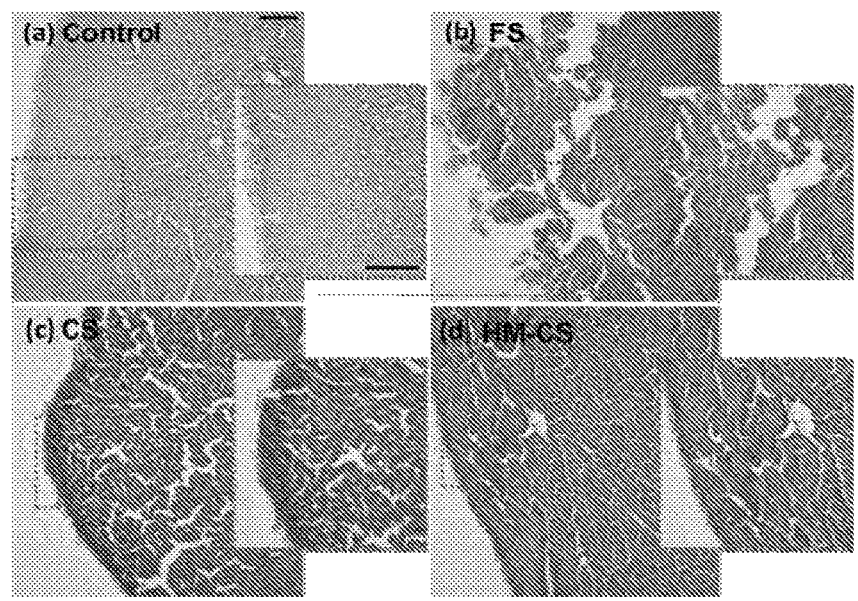
FIG. 6. Liver tissue histopathology at 6 week timepoint. In (a), no treatment control shows control tissue showing normal cell architecture; the arrow shows white blood cells and macrophages on end, demonstrating healthy tissue reconstruction. In (b), Tisseel®-treated tissues have potential biliary retention. In (c), CS treated animals demonstrate both white cell/macrophages, as well as biliary retention. In (d), HM-CS treated animals show tissue repair phenotype similar to control. Scale bars=100 µm.

Tissue histopathology images are shown in FIG. 6. In the negative control (FIG. 6a), normal cell architecture is observed; white blood cells and macrophages can be seen on tissue boundaries, demonstrating healthy tissue reconstruction. In contrast, for FS (FIG. 6b), stunted tissue reconstruction with potential biliary retention at tissue boundaries. The CS group demonstrated a combination of normal white blood cell and macrophage infiltration, also with mild biliary retention at tissue boundaries (FIG. 6c).

6-week survival was the primary endpoint for the current pre-clinical study. Both chitosan and hydrophobic chitosan derivatives demonstrated a basic utility as internal-use absorbable materials given that all animal survived the intervention at this timepoint. Given that the material breaks down primarily by the activity of lysozymes in the body, the survival prognosis for the material is favorable.

EXAMPLE

The experiments described below compare the long-term in vivo safety of HM-CS relative to a commonly used fibrin sealant (FS), Tisseel® (Baxter), which has not been conducted before.

64 Sprague-Dawley rats (275-325 g obtained from Charles River Laboratories) were randomly assigned to control (n=16) or experimental (n=48) groups. Samples of the test materials (HM-CS (n=16), CS (n=16) and FS (n=16)) applied to a non-lethal liver excision (0.4±0.3 g of the medial lobe) in rats were left inside the abdomen to degrade. Animals were observed daily for signs of morbidity and mortality. Surviving animals were sacrificed at 1 and 6 weeks; the explanted injury sites were microscopically assessed.

HM-CS was synthesized by attaching n-palmitoyl tails to the chitosan backbone via reaction with palmitic anhydride.

The procedure is similar to that reported in earlier work and it also follows those described in the literature. The degree of hydrophobic substitution follows the reaction stoichiometry and here it was fixed at 1.5 mol % of the available amine groups. HM-CS or CS were dissolved in 0.2 M acetic acid solution at 2 wt % (w/v). Sodium bicarbonate was dissolved in water a 0.3M.

A double barrel syringe chamber was capped to prevent leakage of fluid. 2 mL of polymer solution, either CS or HM-CS, at 2.0 wt % was added to one chamber of a double barrel syringe (purchased from J. Dedoes) and the other chamber was filled with 2 mL of sodium bicarbonate solution. The syringe's plungers were inserted in the barrels and pushed until resistance was felt due to hydrostatic pressure of the fluid. Finally, the cap was removed, and the mixing tip was fastened onto the chamber port.

Sixty-four eight-week-old Sprague-Dawley rats (275-325 g obtained from Charles River Laboratories) were randomly assigned to control or experimental groups. Sixteen animals served as controls, receiving a midline laparotomy and partial hepatectomy but no applied hemostatic agent. The remaining 48 animals were randomized across three experimental groups that received one of three possible hemostatic agents: a fibrin-based agent (Tisseel®), an unmodified chitosan agent (CS), or a hydrophobically-modified chitosan agent (HM-CS). Half of the animals were euthanized one-week post-surgery and the remainder were euthanized at six weeks post-surgery. All rats were weighed pre-operation, and anesthetized using isoflurane gas (induced at 4% and maintained at 2%). The animals were placed on a heated pad to maintain a body temperature of 37° C., with the abdomen exposed underneath a sterile surgical drape. The surgical site was aseptically prepared three times using alternating chlorohexidine and ethanol swabs, and lidocaine was administered along the incision site on the abdomen. A ventral midline approach to the abdominal cavity was performed, and the medial liver lobe was identified. A sterile ruler was used to mark the medial liver lobe 0.5 cm from the distal end of the lobe, and the distal end was sharply excised according to that marking.

Sixty seconds after the partial hepatectomy was performed, animals in the experimental groups received the respective hemostatic agent delivered directly to the injury site via syringe applicator, and the rat was left under anesthesia for 1 h with the abdominal cavity open to allow for formation of a stable clot. Sterile 4×4 gauzes were weighed prior to surgery, then utilized to collect hemorrhage from the abdomen and re-weighed to determine amount of blood loss that occurred. FIG. 1 shows the excision area treated with each agent immediately after application. After 1 hour, the abdominal cavity was closed utilizing a simple continuous pattern of absorbable suture in the abdominal body wall, and an intradermal pattern of absorbable suture for skin closure. Triple antibiotic cream was layered on top of the sutured skin. Buprenorphine (1 mg/kg) was injected subcutaneously before animals were removed from anesthesia and individual rats were placed into new, clean cage under a heat lamp to recover. Animals were returned to the animal facility after recovery, housed with free access to food and water and under regulated conditions of temperature, relative humidity, and illumination (12 h light/dark cycles).

Animals were observed every 12 h for the first 72 h post-surgery, and once a day over the following two weeks. One week and six weeks post-surgery, animals were anesthetized using 5% isoflurane gas and transcardially perfused with 200 mL saline rinse (with 10 units/mL heparin, pH 7.4) followed by 200 mL of 4% paraformaldehyde in PBS. In the ISO standard for implantation testing of medical devices, time points of 1, 4 and 13 weeks are evaluated. In this initial survival safety study, we observe 1 and 6 week time points, because they provide screening confidence on the outcomes of (a) mortality, (b) morbidity, (c) tissue reactivity and (d) adhesions. While we ultimately care about safety over the period of years/decades, for a degradable implantable material, we will understand critical outcomes in these four areas in a fairly short period of time. The 1 and 6 week time points give us a screening framework to quickly understand the utility of a material for implantable biosurgical purposes. Prior to perfusion, peripheral blood was collected from the rats for evaluation of global inflammation. The injury site of the medial lobe was removed, along with a section of an untouched lobe.

Adhesions.

Upon euthanasia, and the subsequent re-opening of the abdomen, adhesions between the liver and surrounding tissues were noted. Adhesions could be categorized as filmy, thick or dense, and the strength of adhesions would be semi-quantitatively scored from 0 to 4, according to the following separation conditions utilizing surgical tweezer (0=no adhesion, 1=mild adhesion, easy to separate, 2=moderate adhesion, requires light force to separate, 3=marked adhesion, requires significant force to separate, 4=severe adhesion, cannot be separated without resection using scalpel blade). Only six animals from each cohort underwent adhesion analysis.

Tissue Processing for Histology.

Liver tissue samples, stored in 10% neutral buffered formalin after necropsies, were processed by standard paraffin embedding methods and sectioned using a microtome (info) into 2-3 µm thick sections and placed onto glass slides. Paraffin-embedded sections were stained with standard hematoxylin & eosin solutions. Sections were observed under the microscope for white blood cells and macrophages on tissue boundaries, as these cell types indicate normal tissue reconstruction.

Procedure and Statistics.

Animals were assigned to treatments according to a random number table. Treatment groups were designated as following: (1) HM-CS, (2) CS and (3) FS. The CS foam was a placebo foam and differed from the HM-CS in that hydrophobes are grafted along the backbone of the chitosan. The investigators were blinded to treatment. The weight of the excised median lobe divided by the preinjury total body weight of the rat was used as a measure of the reproducibility of the injury. Blood loss was corrected for body weight (mL/kg). All measures are presented as mean±standard deviation (SD). For measures with differences between group means, direct comparisons of the HM-CS groups with the CS and FS groups were performed using a student's unpaired t-test. Statistical significance was assigned at a greater than 95% confidence level (P<0.05).

All animals (64/64) survived both the 1 and 6 week time-points without signs of morbidity. Histological examination showed a comparable pattern of degradation for the various test materials. FS remnants and significant adhesions to neighboring tissues were observed at 6 weeks. Residual CS and HM-CS were observed at the 6 weeks with fatty deposits at the site of injury. Minimal adhesions were observed for CS and HM-CS.

The internal safety observed in the HM-CS test group after abdominal implantation indicates that injectable HM-CS expanding foam may be an appropriate internal-use hemostatic candidate.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A method for reducing adhesion between organs and tissues, comprising:
applying a flowable solution of a hydrophobically-modified chitosan, wherein hydrophobic modifications of chitosan are selected to allow for adherence to tissue, cohesiveness of the composition upon application to tissue, and degradation after application; wherein the hydrophobically-modified chitosan is applied to surfaces of tissues or organs within a surgical site either before, during, and/or after a surgical procedure, wherein the hydrophobically-modified chitosan reduces adhesion between organs or tissues after surgery; and wherein the hydrophobically modified chitosan has about 10% to 50% of available functional groups occupied by hydrophobic groups, and wherein the hydrophobic groups comprise a C1 to C4 hydrocarbon group and a hydrocarbon group of greater than C6.

2. The method of claim 1, wherein the surfaces comprise parenchymal surfaces.

3. The method of claim 1 wherein the surgical procedure is performed in an animal.

4. The method of claim 1, wherein the surgical procedure is performed in a human subject.

5. The method of claim 1, wherein the degradation occurs within two weeks.

6. The method of claim 1, wherein the degradation occurs within a period of two months, one month, one week, or within two days.

7. The method of claim 1, wherein the C1 to C4 hydrocarbon group is present at 5:1 to 25:1 with respect to hydrocarbon groups of C6 or greater.

8. The method of claim 7, comprising a hydrocarbon group of from C6 to C12 and a hydrocarbon group of from C16 or C18.

9. The method of claim 8, comprising C8 hydrocarbons and C14, C16, and/or C18 hydrocarbons.

10. The method of claim 7, wherein the hydrophobic groups comprise a C6 to C12 hydrocarbon and a C16 to C28 hydrocarbon.

11. The method of claim 10, wherein the C6 to C12 hydrocarbons are present at a ratio of from 5:1 to 20:1 with respect to C16 to C28 hydrocarbons.

12. The method of claim 1, wherein the hydrophobic groups comprise a C1 to C4 hydrocarbon group, a C6 to C12 hydrocarbon, and a C16 to C28 hydrocarbon.

13. The method of claim 1, wherein the flowable solution is antibacterial.

14. The method of claim 1, wherein the flowable solution creates an antibacterial barrier when applied to a tissue.

* * * * *